United States Patent [19]
Current

[11] Patent Number: 4,625,050
[45] Date of Patent: Nov. 25, 1986

[54] ETHER HOMOLOGATION TO ESTERS AND ALCOHOLS USING A HETEROGENEOUS SULFIDED CATALYST

[75] Inventor: Steven P. Current, Novato, Calif.

[73] Assignee: Chevron Research Company, San Francisco, Calif.

[21] Appl. No.: 507,304

[22] Filed: Jun. 23, 1983

[51] Int. Cl.$^4$ .............. C07C 29/36; C07C 31/08; C07C 67/37; C07C 69/14

[52] U.S. Cl. .............. 560/232; 260/410.9 R; 568/907

[58] Field of Search .............. 560/232, 265; 260/410.9 R; 568/876, 885, 907

[56] References Cited

U.S. PATENT DOCUMENTS 2,593,440 4/1952 Hagemeyer et al. .............. 560/232
4,189,441 2/1980 Braca et al. .............. 568/907
4,304,946 12/1981 Isogai et al. .............. 568/902
4,431,835 7/1981 Gauthier-Lafaye et al. .............. 560/105
4,482,497 11/1984 Rizkalla .............. 560/413

FOREIGN PATENT DOCUMENTS 34374 8/1981 European Pat. Off. .............. 568/907

Primary Examiner—Vivian Garner
Attorney, Agent, or Firm—T. G. DeJonghe; C. J. Caroli

[57] ABSTRACT

A process for the conversion of dialkyl ethers to homologous carboxylic acid esters and alcohols which comprises reacting a dialkyl ether having from two to about twenty carbon atoms with hydrogen and carbon monoxide in the presence of a heterogeneous sulfided catalyst comprising nickel, optionally in admixture with a co-catalyst selected from the elements of Group VI-B of the Periodic Table.

5 Claims, No Drawings

ETHER HOMOLOGATION TO ESTERS AND ALCOHOLS USING A HETEROGENEOUS SULFIDED CATALYST

BACKGROUND OF THE INVENTION

The present invention is concerned with a process for the homologation of ethers to esters and alcohols. More specifically, the present invention involves a process for the conversion of dialkyl ethers to homologous carboxylic acid esters and alcohols by reaction of the ether with hydrogen and carbon monoxide in the presence of a heterogeneous suflided catalyst.

An article by M. Hidai et al. in Bull. Chem. Soc. Japan, volume 55, pages 3951-52 (1982) describes the homologation of methyl esters, in particular the conversion of methyl acetate to ethyl acetate, with synthesis gas in the presence of a homogeneous ruthenium-cobalt catalyst and a methyl iodide promoter.

European Patent Application Publication No. 0031606 A 1 describes the preparation of carboxylic acids and esters from carboxylic acid esters having one less carbon atom, carbon monoxide and hydrogen in the presence of a catalyst containing a ruthenium compound, a Group II metal iodide and/or bromide and a further Group VIII metal compound.

European Patent Application Publication No. 0031784 A2 describes the preparation of alkyl carboxylates from lower homologs by reaction with carbon monoxide and hydrogen using a ruthenium, cobalt and iodide catalyst system.

European Patent Application Publication No. 0046128 A1 describes the hydrocarbonylation and/or carbonylation of alkyl carboxylates in the presence of ruthenium, cobalt, vanadium and an iodide promoter.

U.S. Pat. No. 2,623,906 discloses that at pressures above 1,000 atmospheres and in the presence of a cobalt catalyst, primary, secondary and tertiary alcohols react with synthesis gas to form glycol ethers and monohydric alcohols containing at least one more carbon atom per molecule than the original alcohol reactant.

U.S. Pat. No. 3,285,948 discloses that an improved yield of ethanol from methanol can be obtained by conducting the synthesis gas homologation reaction in the presence of a cobalt catalyst which is promoted with iodine and a metal halide selected from ruthenium halide and osmium halide.

U.S. Pat. No. 4,111,837 discloses a process for producing ethanol which comprises reacting methanol with carbon monoxide and hydrogen in the presence of a catalyst consisting essentially of a methanol-soluble cobalt carbonyl and methanol-insoluble rhenium metal.

U.S. Pat. No. 4,304,946 discloses a process for producing ethanol from methanol, carbon monoxide and hydrogen which comprises conducting the reaction in the presence of a cobalt sulfide or a mixture of a cobalt sulfide and at least one of a nitrogen-containing compound and a phosphorus compound.

SUMMARY OF THE INVENTION

The present invention relates to a process for the conversion of dialkyl ethers to homologous carboxylic acid esters and alcohols which comprises reacting a dialkyl ether having from tow to about twenty carbon atoms with hydrogen and carbon monoxide at a temperature in the range of about 150° C. to 350° C. and a pressure in the range of about 500 psig to 5,000 psig in the presence of a heterogeneous sulfided catalyst comprising nickel, optionally in admixture with a co-catalyst selected from the elements of Group VI-B of the Periodic Table.

Among other factors, the present invention is based on my discovery that dialkyl ethers can be converted to useful oxygenated products having at least one more carbon atom than the starting ether in improved yield and selectivity by utilizing a heterogeneous sulfided catalyst system.

An advantage of the present process lies in the fact that the heterogeneous catalyst employed is easier to separate from the reaction products than the homogeneous catalysts of the prior art.

In addition, it has been found that the present process does not require any soluble promoters or co-catalysts. This is particularly advantageous, since the absence of a halide promoter in the system obviates the need for expensive corrosion resistant equipment.

Oxygen-containing carbon compounds obtained with high selectivity in the process of the invention are carboxylic acid esters and alcohols or the secondary products which may be formed therefrom under the reaction conditions in a subsequent reaction, for example, reduction, hydrolysis, condensation or dehydration.

DETAILED DESCRIPTION OF THE INVENTION

Illustrative of a typical batch procedure, the dialkyl ether is charged to a high pressure reactor, and then there is introduced a heterogeneous sulfided catalyst system comprising nickel and, optionally, an element of Group VI-B of the Periodic Table. The reactor is pressurized with a mixture containing carbon monoxide and hydrogen and heated for a suitable length of time to give the desired conversion. Liquid and gaseous products and reactants can be easily separated from the catalyst by filtration, distillation or other methods. Unreacted starting materials can be recycled. The products can be isolated by a number of known methods, including distillation. In some cases it may be advantageous to further process the products. For example, methyl acetate can be easily hydrolyzed to acetic acid.

The process of the present invention can also be run in a continuous fashion. This is particularly advantageous as the catalyst is not soluble in the reaction medium. A number of reactor configurations are suitable including fixed and fluid beds, slurry beds and stirred tank reactors. As with a batch reaction, unreacted starting materials can be easily recycled and, if desired, the products can be further processed.

The dialkyl ethers suitable for use in the present invention will generally contain from two to about twenty, preferably two to six, carbon atoms. Suitable dialkyl ethers includes dimethyl ether, diethyl ether, dipropyl ether, methyl ethyl ether, methyl propyl ether, and the like. A preferred dialkyl ether is dimethyl ether. If desired, the reactant dialkyl ether may be diluted with an ether-miscible solvent such as dioxane, tetrahydrofuran, N-methylpyrrolidinone, and the like. when dimethyl ether is used as the starting ether, the reaction products predominantly fromed are methyl acetate and ethanol, with lesser amounts of methyl formate and propanol.

The heterogeneous sulfided catalyst system employed in the present process comprises a composite of sulfides of a nickel component and, optionally, a Group VI-B component. Group VI-B co-catalysts suitable for admixture with the nickel component include chromium, molybdenum and tungsten. A particularly preferred catalyst system comprises nickel and molybdenum. In addition, the catalyst system may optionally contain phosphorus or silicon.

In carrying out the reaction, it is usually desirable, although not essential, to place the catalyst on a support. Various supports suitable for use in the process are described in the prior art. Generally, the support should be a solid, inert material which is relatively insoluble in the solvent employed. Suitable supports include various treated or untreated organic and inorganic supports. Included among these are synthetic and naturally occurring polymers, alumina, silica, titania, silica-alumina, zeolites, glass, carbon, and the like. Particularly preferred supports are alumina and silica-alumina.

The metals may be added to the support using a number of methods known to the art such as by impregnation, co-precipitation, and the like. The method of loading the catalyst on the support will depend on the nature and composition of the support. Generally, the most convenient method of depositing the metals on the support is by adding a solution of metal salts to the support and subsequently converting them to an insoluble form.

An especially suitable catalyst precursor may be prepared by impregnating alumina with an aqueous or organic solution of the metal salts, either together or sequentially, followed by drying and calcining to give the metal oxides.

The catalyst may be converted to its active sulfide form by any of a number of conventional procedures. Treatment with hydrogen sulfide or other sulfur-containing compounds such as carbon disulfide, dimethyl disulfide or sulfur, in the presence of hydrogen or synthesis gas is effective. This treatment can be either prior to or concurrent with the ether carbonylation reaction.

In the process of the present invention dialkyl ethers are reacted with carbon monoxide and hydrogen (synthesis gas). Synthesis gas produced by the reaction of carbonaceous material with water is suitable. Mixtures of carbon dioxide and hydrogen, carbon monoxide and water, and the like, may also be employed. Whether introduced orginally, or produced in situ under processing conditions, the reaction elements of carbon monoxide and hydrogen are required.

The relative molar quantities of carbon monoxide and hydrogen present during the reaction can vary in the range between about 10:1 and 1:10, and preferably in the range between about 3:1 and 1:3. An inert diluent gas such as nitrogen or helium may be included if desired.

The carbonylation reaction requires a relatively high pressure for optimum selectivity and yield of product. The pressure is maintained in the range between about 500 psig and 5,000 psig, and preferably in the range between about 800 psig and 2000 psig.

The reaction is conducted at a temperature in the range between about 150° C. and 350° C., and preferably in the range between about 190° C. and 290° C.

The time that the reactants are in contact with the catalyst will be dependent, among other factors, on the temperature, pressure, ether reactant, catalyst, reactor configuration and the desired level of conversion.

The solid catalyst can be easily separated from the generally liquid and gaseous reaction products and unreacted starting materials by, for example, filtration, centrifugation, settling out or distillation. The catalyst can be reused in subsequent reaction. Unreacted starting materials can be separated from reaction products and are suitable for recycle in the process.

The products of the reaction, which can be isolated by a number of well-known methods such as distillation, are generally useful as solvents or chemical intermediates. In some cases it may be advantageous to further process the reaction products by well-known means to other useful products. For example, methyl acetate can be hydrolyzed to acetic acid.

The following examples are provided to illustrate the invention in accordance with the principles of this invention but are not to be construed as limiting the invention in any way except as indicated by the appended claims.

EXAMPLE

Example 1

An 18 ml stainless steel reactor was charged with 3.9 g of dimethyl ether and 0.5 g of a catalyst comprising nickel (6%) and molybdenum (15%) oxides, supported on silica-alumina, that had been pretreated with 10% hydrogen sulfide in hydrogen at 325° C. Also included was 0.10 ml of 1,4-dioxane to serve as an internal standard for gas chromatography analysis. The reactor was pressurized to 900 psi with a 2:1 mixture of hydrogen and carbon monoxide and heated with shaking at 240° C. for four hours. The reactor was then cooled in an ice bath and vented. The contents were diluted with methanol. Analysis indicated methyl acetate (1.8 mmol) and ethanol (0.5 mmol) as major products. Also formed in lesser amounts were methyl formate and propanol.

What is claimed is:

1. A process for the conversion of dialkyl ethers to homologous carboxylic acid esters and alcohols which comprises reacting a dialkyl ether having from two to about twenty carbon atoms with hydrogen and carbon monoxide at a temperature in the range of about 150° C. to 350° C. and a pressure in the range of about 500 psig to 5,000 psig in the presence of a heterogeneous sulfided catalyst comprising a composite of sulfides of a nickel component and a Group VI-B element component cocatalyst and in the absence of a halide promoter.

2. The process according to claim 1, wherein the co-catalyst is molybdenum.

3. The process according to claim 1, wherein the sulfided catalyst is present on a support.

4. The process according to claim 3, wherein the support is alumina or silica-alumina.

5. The process according to claim 1, wherein dimethyl ether is converted to methyl acetate and ethanol.

* * * * *